(12) United States Patent
Su

(10) Patent No.: US 10,375,957 B2
(45) Date of Patent: Aug. 13, 2019

(54) FLUID BAIT FORMULATIONS AND THEIR USE WITH ACTIVE TERMITE INFESTATION

(71) Applicant: University of Florida Research Foundation, Incorporated, Gainesville, FL (US)

(72) Inventor: Nan-Yao Su, Davie, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 14/766,820

(22) PCT Filed: Mar. 4, 2014

(86) PCT No.: PCT/US2014/020316
§ 371 (c)(1),
(2) Date: Aug. 10, 2015

(87) PCT Pub. No.: WO2014/149684
PCT Pub. Date: Sep. 25, 2014

(65) Prior Publication Data
US 2016/0000073 A1 Jan. 7, 2016

Related U.S. Application Data

(60) Provisional application No. 61/798,972, filed on Mar. 15, 2013.

(51) Int. Cl.
| | |
|---|---|
| *A01N 37/46* | (2006.01) |
| *A01M 1/20* | (2006.01) |
| *A01M 1/24* | (2006.01) |
| *A01N 25/00* | (2006.01) |

(52) U.S. Cl.
CPC .............. *A01N 37/46* (2013.01); *A01M 1/20* (2013.01); *A01M 1/24* (2013.01); *A01N 25/006* (2013.01)

(58) Field of Classification Search
CPC ........... A01M 1/24; A01M 1/20; A01N 25/06; A01N 25/02; A01N 41/06; A01N 43/40; A01N 43/54; A01N 43/90; A01N 47/02; A01N 47/34; A01N 47/36; A01N 51/00; A01N 59/14; A01N 37/46
See application file for complete search history.

(56) References Cited

U.S. PATENT DOCUMENTS

| | | | |
|---|---|---|---|
| 5,886,221 A | 3/1999 | Sbragia et al. | |
| 6,172,051 B1 * | 1/2001 | Renello ................ | A01N 25/006 424/84 |
| 6,195,934 B1 | 3/2001 | Megargle et al. | |
| 6,245,327 B1 * | 6/2001 | Faehl .................... | A01N 25/006 424/405 |
| 6,352,703 B1 * | 3/2002 | Henderson ........... | A01N 25/006 424/405 |
| 6,370,812 B1 | 4/2002 | Burns et al. | |
| 6,370,814 B1 | 4/2002 | Curtis et al. | |
| 6,397,516 B1 | 6/2002 | Su | |
| 6,773,727 B1 | 8/2004 | Rojas et al. | |
| 8,021,675 B2 * | 9/2011 | Graham ............... | A01N 25/006 424/410 |
| 2006/0027361 A1 * | 2/2006 | Hanson .................. | C10L 1/003 166/261 |
| 2007/0148202 A1 | 6/2007 | Primo Yufera et al. | |
| 2010/0083556 A1 * | 4/2010 | Wright .................. | A01M 1/026 43/1 |
| 2011/0225875 A1 | 9/2011 | Lloyd | |

FOREIGN PATENT DOCUMENTS

| | | |
|---|---|---|
| GB | 1561901 | 3/1980 |
| WO | WO 2010/021687 A1 | 2/2010 |

OTHER PUBLICATIONS

Hiraki et al. Eng. Abstract, JP 05246883 A.*
Esenther, G.R. et al., "Termite attractant from fungus-infected wood," *Science*, 1961, 134(3471):50.
Cornelius, Mary L. et al., "Effect of Summon Preferred Food Source on Feeding, Tunneling, and Bait Station Discovery by the Formosan Subterranean Termite (Isoptera: Rhinotermitidae)," *J. Econ. Entomol*, 2005, 98:502-08.
Su, Nan-Yao. "Field Evaluation of a Hexaflumuron Bait for Population Suppression of Subterranean Termites (Isoptera: Rhinotermitidae)," *J. Econ. Entomol.*, 1994, 87(2):389-397.
Su, Nan-Yao. "Hermetically Sealed Baits for Subterranean Termites (Isoptera: Rhinotermitidae)," *J. Econ. Entomol.*, 2007, 100:475-482.
Su, Nan-Yao. "Biological activities of a bait toxicant for population management of subterranean termites (Isoptera: Rhinotermitidae)," *Recent Advances in Sustainable Household, Structural and Residential Pest Management*, 2007, p. 1.
Su, Nan-Yao et al., "A Method to Access, Trap, and Monitor Field Populations of the Formosan Subterranean Termite (Isoptera: Rhinotermitidae) in the Urban Environment," *Sociobiology*, 1986, 12(2):299-304.
Su, Nan-Yao et al., "Laboratory Evaluation of Two Chitin Synthesis Inhibitors, Hexaflumuron, and Diflubenzuron, as Bait Toxicants Against Formosan and Eastern Subterranean Termites (Isoptera: Rhinotermitidae)," *J. Econ. Journal*, 1993, 86(5):1453-1457.

(Continued)

*Primary Examiner* — Blessing M Fubara
(74) *Attorney, Agent, or Firm* — Saliwanchik, Lloyd & Eisenschenk

(57) ABSTRACT

The subject invention provides fluid formulations for use in controlling a population of a pest once it has been detected. Specifically, the subject invention pertains to a fluid bait formulation comprising a feed medium impregnated with at least one active ingredient and a liquid carrier. The invention is based on the concept of providing a unique fluid bait formulation that can be injected into a termite infestation site, where an effective amount of AI(s) is presented to the termite population, even following dehydration of the formulation, to control the termite population.

20 Claims, 3 Drawing Sheets

(56) References Cited

OTHER PUBLICATIONS

Su, Nan-Yao et al., "A Monitoring/Baiting Station to Detect and Eliminate Foraging Populations of Subterranean Termites Isoptera: Rhinotermitidae) Near Structures," *J. Econ. Entomol*, 1995, 88(4):932-936.

Su, Nan-Yao et al., "Remedial baiting with hexaflumuron in above-ground stations to control structure-infesting populations of the Formosan subterranean termite (Isoptera: Rhinotermitidae)," *J. Econ. Entomol.*,1997, 90(3):809-817.

Su, Nan-Yao., et al., "Control of subterranean termites (Isoptera: Rhinotermitidae) using commercial prototype aboveground stations and hexaflumuron baits," *Sociobiology*, 2001, 37:Abstract.

Su, Nan-Yao, et al., "Characterization of tunneling geometry of subterranean termites (Isoptera: Rhinotermitidae) by computer simulation," *Sociobiology*, 2004, 44:Abstract.

\* cited by examiner

FLUID BAIT FORMULATIONS AND THEIR USE WITH ACTIVE TERMITE INFESTATION

CROSS-REFERENCE TO A RELATED APPLICATION

This application is a National Stage Application of International Application Number PCT/US2014/020316, filed Mar. 4, 2014; which claims the benefit of U.S. provisional application Ser. No. 61/798,972, filed Mar. 15, 2013, both of which are incorporated herein by reference in their entirety.

BACKGROUND OF THE INVENTION

Subterranean termites construct an extensive foraging gallery beneath the soil surface. A single colony may contain several million termites with foraging territory extending hundreds of feet. Because subterranean termites are cryptic creatures, their presence is not normally known until after some damage, foraging tubes, or live termites (such as swarmers) are found.

There are two general types of termite bait products on the market for controlling termites. One type is the in-ground (IG) system. As described in U.S. Pat. No. 6,397,516, IG systems typically comprise of durable monitoring stations containing monitoring wood pieces that are installed in soil around a house to intercept termites. When termites are found in the stations through a routine monitoring, the infested wood pieces are replaced with baits containing active ingredients (AIs) to kill the termites.

One current IG system utilizes durable baits to bypass the monitoring phase, but baits are still applied in soil to intercept subterranean termites (Su 2007). It is desirable that AIs be non-repellent to induce termite feeding of baits, and be slow-acting so that termites may carry the AIs back and share them with nestmates. Termites are social insects, and members of a colony share interconnected gallery systems extending up to 300 feet. Baits that are consumed by termites from a single station are spread to the entire colony leading to the colony elimination. This IG bait system is used for both preventive and remedial control.

Another type of bait system is intended for remedial control only, and is designed to be placed over active infestation of termites so that termites may come into bait stations to feed on baits. Since the bait system is typically used in the above-ground portions of a structure, it is usually referred to as an "above-ground" (AG) bait system. U.S. Pat. No. 6,370,812 described one such AG bait system comprised of a bait box with one open side mounted on a wall that is infested with termites. Baits are placed in contact with termites in the box before it is closed with a lid. This arrangement allows termites to enter the AG station to consume baits. However, one requirement for successful termite control with an AG system is a completely sealed AG station to prevent air flow, where airflow discourages termites from entering the AG station. Placement of the rigid AG bait box on uneven surfaces without creating a gap can be challenging. Often, where there is a gap between the flat surface of the open side of the AG box, the uneven surface has to be sealed off with additional tapes or other means in order to encourage termite entry into the AG box.

U.S. Pat. Nos. 6,195,934 and 6,370,814 attempted to solve the placement problems by providing unique openings and configurations of AG bait boxes so that they can more precisely intercept termites in their foraging tubes without creating too much gaps. Another solution was to use a flexible enclosure as a bait container so that it may be adhered over surfaces of various contours (Su et al. 1997). Due to the tamper-proof concerns, however, the flexible AG stations with soft enclosures are currently not commercially available.

Another problem with the current AG bait system is that it can be unsightly and intrusive because the AG stations are usually installed in a house visible to residents who dislike to be reminded of the presence of termites, even those inside the AG boxes. Moreover, the bulky AG station may not be installed over the active termite infestation in a tight spot where no room is available to accommodate the AG box.

Fluid formulations containing AIs are available for controlling termite infestations. These formulations, however, do not contain feeding medium. Instead they are intended to be injected into wooden cavities to deposit AIs on the inner surface of the wood cavities to form a bait by using the wood as the feeing medium. When placed in the wooden cavities, the AI-containing fluid formulations dehydrate when adjacent materials, such as wood, absorb the liquid phase of the formulations. This leaves an unpredictable AI concentration on the wood surface, depending on the existing wood moisture and relative humidity. Repellency and feeding deterrence of most AIs are concentration-dependent, and unless they are properly formulated, dehydrated baits generally will not satisfy the necessary non-repellency and slow-acting characteristics needed to control and kill termites.

U.S. Publication No. 2011/0225875, for example, describes a wooden bait system with reservoirs to receive liquid insecticides, such as borates, before the treated bait is placed on or in soil to intercept termites. Because the liquid formulations do not contain feeding medium, and instead the feeding medium is the treated wood, when the liquid in the borate solution is absorbed by the wood, the treated wood surface in the reservoirs may not contain a desired concentration of the borate that is both non-repellent and slow-acting for controlling termites.

Australian Patent No. 1,597,293 (the '293 patent) and a corresponding Great Britain Patent, No. 1,561,901, describe a method which involves mixing termiticide with a food matrix comprising cellulose and a binding agent to form a past-like bait. The '293 method, however, did not address the problem of introducing sufficient quality of bait into termite galleries through small and restricted injection port since only a limited quality of past-like bait may be smeared or pushed into the galleries if the access port is restricted. The method described in the '293 patent relies on the termite ingesting the termiticide along with the matrix, then returning to the colony to introduce the termiticide to other termites through the natural process of trophallaxis (food exchange between termites). Furthermore, the '293 method fails to ensure that the moisture will remain in the food matrix/termiticide combination to ensure proper concentration of termiticide is presented to termites. Over time, dehydration of the '293 mixture affects the concentration of the termiticide, which will also affect the repellency and activity characteristics of the termiticide. Moreover, even a moistened sawdust-agar food matrix will desiccate and degrade within a few days when placed in a dry soil and become unpalatable to termites. Thus, the '293 has no means for ensuring the termiticide will be transmitted to a termite infestation, let alone provide a method for controlling the infestation.

Accordingly, a fluid bait matrix is needed to solve the above-mentioned problems associated with current bait matrices used for controlling termites.

BRIEF SUMMARY

The present invention provides materials and methods for controlling termite infestations. In particular, the invention pertains to a fluid bait formulation comprising a feed medium impregnated with at least one AI and a liquid carrier.

The present fluid bait formulation can be used against termite pests of family Rhinotermitidae, Kalotermitidae, or Termitidae.

The feed medium comprises particles of material that termites would be attracted to and feed. In one embodiment, a cellulosic material is impregnated with at least one AI. The AI can be any agents that are slow-acting, non-repellent, and the lethal time is dose-independent at proper concentrations, including but not limited to insect growth regulators and/or metabolic inhibitors.

In certain embodiments, the subject fluid bait formulation further comprises a termite attractant to increase the possibility that the termites located within foraging tunnels to which the formulation is applied will consume the AI(s) impregnated feed medium.

In certain embodiments, additives and/or preservatives may be added to the fluid bait formulation. For example, additives for retaining moisture in the formulation and/or preservatives for preventing unwanted decay of the feed medium may be included in the formulation.

The cellulose particles are pre-treated with desired concentrations of AIs. This ensures that when the fluid bait is absorbed by termite galleries, such as damaged wood, the dehydrated feed medium contains proper AI concentrations that are both non-repellent and slow-acting on termites.

In a first aspect, the fluid bait formulation of the invention provides an effective concentration of the AI(s) in the feed medium that is both non-repellent and slow-acting to termites even following desiccation of the formulation.

In another aspect, the present invention takes advantage of the fact that active termite infestations typically contain voids created by termites when they chew through wood or construct galleries in soft materials such as plaster or plastic polymers. In cases where only fragile termite shelter tubes are accessible for bait application, a container preferably made of termite-edible materials may be placed in contact with the active shelter tube, and the fluid bait is placed in the container for termite feeding. The fluid bait formulation of the invention has a viscosity that allows it to be injectable. The viscosity of the fluid bait formulation must allow it to flow in and down to the voids with some of the baits adhering onto inner surface of voids in structures created by termite tunneling or chewing (also referred to herein as termite galleries). In a specific embodiment, the viscosity of a fluid termite bait formulation must allow it to be deployed from a syringe or a caulking gun so as to fill termite galleries without clogging the narrow injection point of the syringe or caulking gun.

In another aspect, a method is provided for controlling an established termite infestation. The method comprises the steps of: providing a fluid bait formulation comprising a feed medium impregnated with at least one AI and a liquid carrier; and injecting the fluid bait formulation into voids in structures created by termites. Because the infested site injected with the fluid bait formulation is normally interconnected with the rest of a termite colony gallery system, the AI(s)-impregnated feed medium of the fluid bait formulation would be consumed and/or carried back by termites of the colony to share with other nestmates. Consumption of the AI(s)-impregnated feed medium would lead to the elimination of the entire colony.

The subject invention has been discovered to be highly effective in controlling even extremely large termite colonies. Advantageously, the subject invention utilizes only very small amounts of AI(s), and the AI(s) are applied in a strictly defined and controlled manner to minimize exposure of the environment and of the user to the AI(s). The use of the AI(s) is confined in terms of the very limited quantity and coverage of the AI(s), and in terms of the period during which the AI(s) would be used.

Thus, another aspect of the invention is to provide an environmentally safe termite control system requiring no complex machinery. The invention provides formulations and methods for delivery of AI(s) to a target termite infestation, wherein relatively simple apparatuses for dispensing the subject fluid bait formulations may be safely used by property owners as well as professional pest management workers.

Advantageously, the disclosed formulations and methods minimize the risk of exposure to persons handling the AI(s) as well as increase AI(s) intake by termites. The formulations and methods of the subject invention can drastically reduce pesticide use in the urban environment.

In another aspect, this invention can be an important part of an integrated termite management approach. The first phase of the integrated termite management approach can be designed to monitor termite activity. No termiticide need be used until termite activity is detected. When activity is detected, the second phase of the integrated termite management approach can be employed, wherein a fluid bait formulation of the invention is used to control the entire termite colony population. Once control is achieved, the monitoring step can be repeated, as can the control step, if necessary, thus providing indefinite protection to the structure or agricultural site of interest.

As described more fully herein, there are a variety of apparatuses which can be utilized to dispense the fluid bait formulations of the subject invention. The precise apparatuses that would be optimal for a particular target pest and environmental setting would be apparent to a person skilled in this art using the teachings provided herein.

The descriptions and teachings that follow primarily focus on the control of termites. Specific methods and formulations for the control of termites are provided, but variations of these methods and formulations and their applicability to pests other than termites would be readily recognized and used by a person skilled in this art.

DETAILED DESCRIPTION

Figure 1:
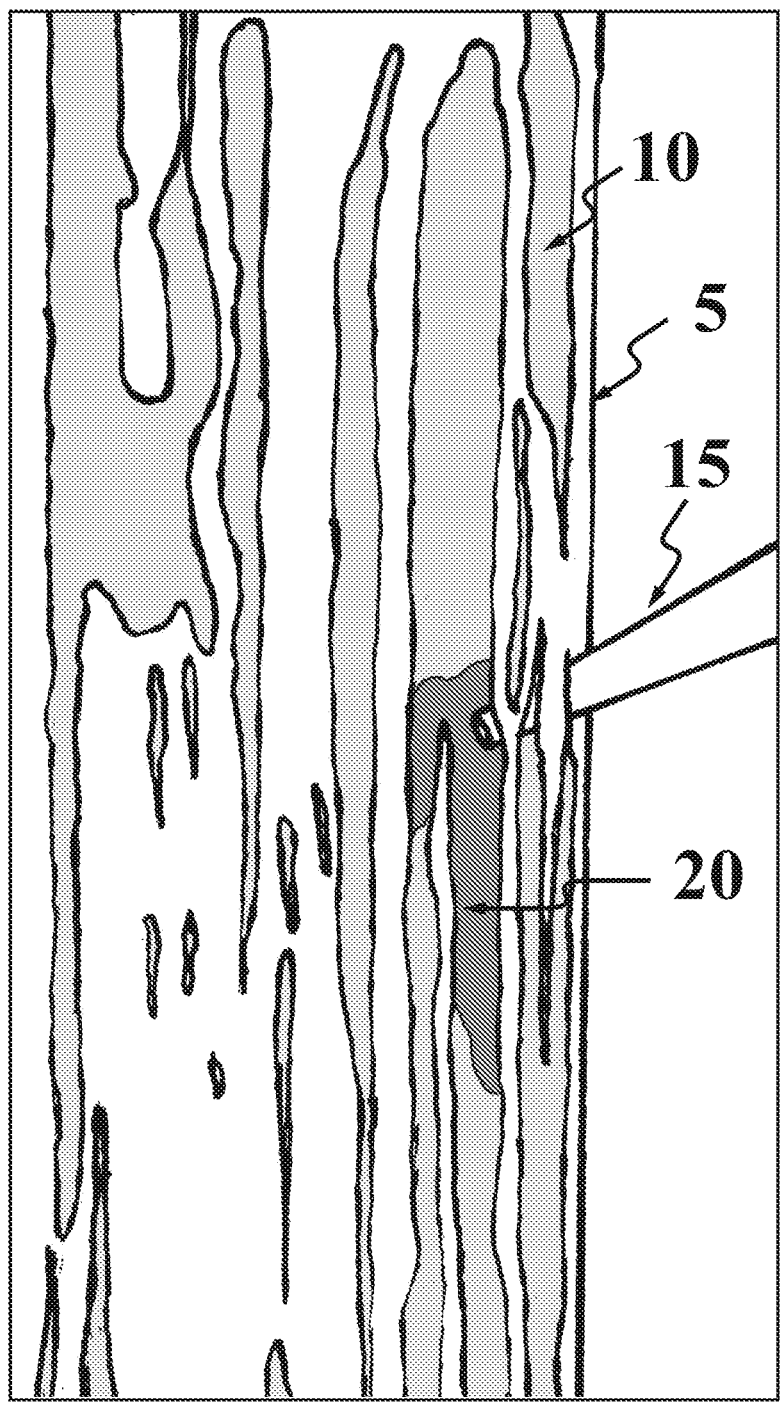
FIG. 1 is a depiction of a cross section of wood (or other similar material) damaged by termites.

The subject invention provides fluid formulations for use in controlling a population of a pest once it has been detected. Specifically, the subject invention pertains to a fluid bait formulation comprising a feed medium impregnated with at least one AI and a liquid carrier. The invention is based on the concept of providing a unique fluid bait formulation that can be injected into a termite infestation site, where an effective (i.e., a lethal AI concentration that is slow-acting and non-repellent) amount of AI(s) is presented to the termite population, even following dehydration of the formulation, to control the termite population.

The subject invention provides a fluid bait formulation that presents to termites within a colony a feed medium impregnated with AI(s) that is toxic to the termites. Preferably, the fluid bait formulation should be delivered into voids created by termite tunneling or feeding or into natural voids (such as internal wall cracks or tree hollows) where termites will likely enter so as to prevent termite infestation.

The fluid bait formulation of the invention has a viscosity that allows it to be injectable. The viscosity of the fluid bait formulation must allow it to flow into and adhere onto the inner surface of voids in structures created by termite tunneling or chewing (also referred to herein as termite galleries). In a specific embodiment, the viscosity of a fluid bait formulation must allow it to be deployed from a syringe or a caulking gun.

In certain embodiments, the viscosity of the fluid bait formulation is between about $(3-4) \times 10^{-3}$ Pa·s to about 100 Pa·s. Preferably, the viscosity of the fluid bait formulation of the subject invention is between about 1-100 Pa·s; more preferably, the viscosity is between about 50-100 Pa·s. In more preferred embodiments, the viscosity is between about 50-60 Pa·s, 60-70 Pa·s, 70-80 Pa·s, 80-90 Pa·s, or 90-100 Pa·s. In alternate embodiments, the viscosity of the fluid bait formulation of the subject invention is between about 1-50 Pa·s. In more preferred embodiments, the viscosity is between about 1-10 Pa·s, 10-20 Pa·s, 20-30 Pa·s, 30-40 Pa·s, or 40-50 Pa·s.

Materials to be used as feed medium may include α-cellulose, wood flour, milled paper or any cellulosic materials in fine powder forms. The particle size or cellulose fiber length, however, have to be large or long enough to contain sufficient quantity of AI(s) after impregnation, and can be fed by termites. A preferred cellulose-containing feed medium is sawdust or wood flour which is not repellent to target termite species.

Suitable AIs that are slow-acting and non-repellent insecticides include insect growth regulators and metabolic inhibitors. The preferred active ingredient will be lethal at concentrations that do not repel the termites. The preferred active ingredient is also capable of being impregnated in the feed medium as described herein. For example, the feed medium may be soaked in AI(s) prior to mixture with a liquid carrier.

Contemplated AIs include, but are not limited to, any one or more of the following: insect growth regulators and metabolic inhibitors. Insect growth regulators may include a broad class of benzoylphenylurea as disclosed in U.S. Pat. No. 5,886,221 (which is incorporated herein by reference in its entirety). Examples of insect growth regulators include chitin synthesis inhibitors such as hexaflumruon, noviflumuron, diflubenzuron, lufenuron, chlorfluazuron, bistrifluron, and triflumruon. Other insect growth regulators include juvenoids or ecdyson agonists, such as those disclosed in U.S. Pat. No. 7,998,496 (which is incorporated herein by reference in its entirety). Slow-acting metabolic inhibitors may include, but are not limited to, borates, sulfluramid, hydramethylnon, ivermectin, fipronil, imidacloprid, and thiamethoxam.

Liquid carriers to be combined with AI(s)-impregnated feed medium can be any liquid useful for suspending powder forms of feed medium. For example, a liquid carrier may include, but is not limited to, water, a methylcell solution, agar solution and/or a gel solution. The final product has to remain in fluid form instead of past-like consistency so that the liquid bait can be injected though a small diameter syringe or a caulking gun. A fluid form is defined here as an entity that does not hold its shape when left in the open, while a past is the one that holds its shape when left in the open. Due to the relatively large particle size and long fiber length of the feed medium, a formulation without sufficient fluid-like consistency tends to clog the injection tip. When the feed medium is made of α-cellulose (average fiber length of ca. 0.06 mm), for example, baits with past-like consistency are squeezed into a solid block when the pressure concentrates at the injection tip, making it impossible to place a sufficient quantity of baits into termite galleries.

Preferably, the fluid carrier, when combined with the AI(s)-impregnated feed medium provides a formulation that does not repel target termites.

In certain embodiments, the subject formulations may include materials for stabilizing and/or maintain the formulation environment. For example, a fluid bait formulation may include a humectant to regulating the moisture content of the formulation. An appropriate humectant can have hygroscopic characteristics.

In certain embodiments, the subject formulations may also include a termite attractant. The termite attractant can be a natural or synthetic product. For example, pheromone mimics, such as brown-rot fungi (*Gloeophyllum trabeum*) extract and its analogs can be used to attract termites to the formulation and feed medium.

In certain embodiments, the subject formulations may also include preservatives for preventing unwanted decay of the feed medium.

An example of the invention disclosed herein uses a fluid bait formulation comprising a feed medium of 90% α-cellulose and 10% wood flour decayed with *G. trabeum*. The feed medium is impregnated with hexaflumuron by mixing acetone solution of hexaflumuron and constantly stirred in a mixer until the total evaporation of acetone so as to yield the final produce of feed medium with 0.5% hexaflumuron (AI wt/wt). Nine parts of the impregnated feed medium are then mixed with one part of 1% methylcel solution to yield 10% dry weight feed medium in 1% methylcel solution. The 1% methylcel solution was viscous enough to suspend particles of feed medium yet remained fluid enough to be injected into termite galleries by using syringes or caulking guns.

According to one embodiment of the invention, a feed medium already impregnated with AI(s) is provided to the user in a kit. The kit could further comprise any one or more of the following: a liquid carrier to be mixed with the AI(s)-impregnated feed medium; an instruction pamphlet with a description regarding how to prepare the fluid bait formulation of the invention; and/or an apparatus for injecting the fluid bait formulation into a termite infestation site.

In a preferred embodiment, a kit is provided comprising a feed medium of 90% α-cellulose and 10% wood flour decayed with *G. trabeum*, where the feed medium is impregnated with hexaflumuron at 0.5% (AI wt/wt), a liquid carrier that is 1% methylcel solution, and an instruction pamphlet providing instructions for mixing the hexaflumuron-impregnated feed medium with the liquid carrier.

In another embodiment, provided is a fluid bait formulation comprising: a feed medium impregnated with AI(s) and a liquid carrier, that is sterilized and/or packaged.

In certain embodiments, where the fluid bait formulation is to be used immediately after it is mixed with a liquid carrier, the feed medium particles do not have to be suspended for a prolonged period, and a lower viscosity liquid carrier, such as 0.5% methylcel or even water, may be used. The proportion of feed medium in the formulation may be increased to 15-20% when the liquid bait formulations are to be injected by using larger diameter apparatuses such as caulking guns.

The subject invention specifically provides a method for controlling a population of termites comprising: providing a fluid bait formulation comprising a feed medium impregnated with at least one AI and a liquid carrier; and injecting the fluid bait formulation into voids in structures created by termites. The termite population may have been detected, for example, following monitoring for termite activity.

With this method, a termite infestation is controlled as a result of termite ingestion and/or contact with an AI(s)-impregnated feed medium that was provided via the fluid bait formulation.

The present fluid termiticide bait formulation can be used against termite pests of family Rhinotermitidae, Kalotermitidae, or Termitidae, but especially desirable against subterranean termite species whose colonies tend to build extensive gallery system, including but not limited to *Coptotermes formosanus, C. gestroi, C. acinaciformis, C. lacteus, C. frenchi, C. crassus, C. niger, Heterotermes aureus, H. tenuis, Odontotermes formosnaus, Reticulitermes flavipes, R. virginicus, R. hageni, R. hesperus, R. speratus, R. flaviceps, R. chinensis, R. fukiensis, R. lucifugus, Nasutitermes exitiosus, N. corniger,* and *N. costalis.*

FIG. 1 provides an example of one method of using a fluid bait formulation of the invention. FIG. 1 is a cross section of wood damaged by termites. The surface of the wood 5 rarely shows signs of termite infestation. Within the wood, termites often construct an extensive gallery system 10 comprised of many voids. A syringe or caulking gun 15 may be used to inject a fluid bait formulation 20 of the invention into the termite gallery 10. Hence the liquid bait formulation has to be fluid enough to be injected through a syringe and yet has to be of sufficient viscosity to be retained within the void to allow termite access to AI(s)-impregnated feed medium and enable termites to spread the feed medium to nestmates to eliminate the colony.

Following is an example that illustrates a system and method for practicing the invention. This example should not be construed as limiting. All percentages are by weight and all solvent mixture proportions are by volume unless otherwise noted.

Example I

Materials and Methods

Figure 2:
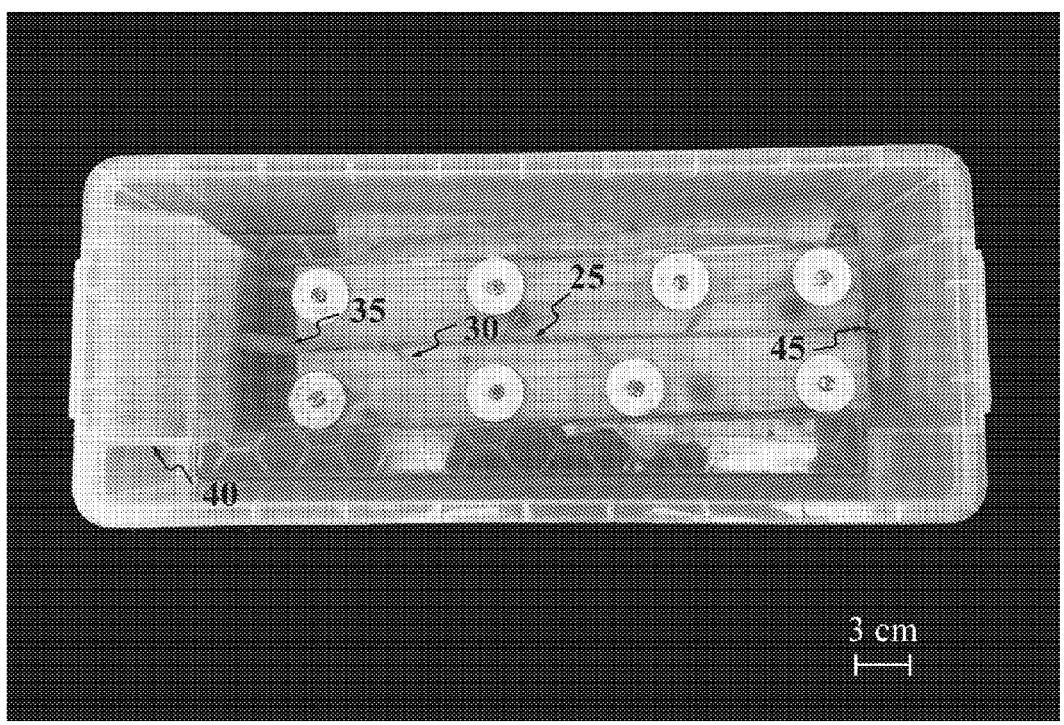
FIG. 2 illustrates an arena composed of spruce boards colonizing termites to which an embodiment of the invention was applied.

Efficacy of the fluid bait formulation was tested in an arena composed of a stack of five spruce (*Picea* sp.) boards (30 cm by 9 cm by 0.4 cm thick each) covered with a sheet of transparent Plexiglas (30 cm by 9 cm by 0.2 cm thick) and tightly secured with eight screws through two steel L-brackets, as shown in FIG. 2. Large washers were placed beneath the crew heads to prevent damaging the Plexiglas, and the steel brackets prevent wooden boards from warping when soaked wet. A 0.5 cm wide main tunnel (0.5 cm deep) 25 was pre-cut at the center of the upper two boards through the entire 30 cm length with four branch tunnels (3 cm long) 30 emerging alternately on both sides at 51° from the main tunnel. The tunnel pattern was provided to simulate that of the subterranean termite galleries (Su et al. 2004). One end of the main tunnel was connected with a Tygon tubing (5 cm by 0.5 cm ID) 35 to a snap-cap plastic container (4 cm by 10.5 cm by 11.5 cm) 40 filled to the 5 cm depth with moistened sand. The other end of the main tunnel 45 was capped with a wooden plug. The arena-container assembly was placed in a large plastic container (42 cm by 17 cm by 12 cm) provisioned with moistened paper at the bottom. The test was done for two subterranean termite species, the Formosan subterranean termite, *C. formosanus*, and the dark southern subterranean termite, *R. virginicus*. Two-hundred fifty workers (plus 25 soldiers for *C. formosanus*, and 3 soldiers for *R. virginicus*) were placed in the snap-on plastic container to allow them to move into the artificial tunnel through the Tygon tubing 35. *C. formosanus* termites were collected from five field colonies (three from New Orleans, La., two from Broward County, Fla.) for testing. Termites of *R. virginicus* collected from three field colonies in Broward County, Fla., plus one colony that has been maintained in the laboratory for over two years were used. Colony origin was used as the replicate, totaling five and four replicates for *C. formosanus* and *R. virginicus*, respectively. The entire assembly was then covered with a plastic lid to maintain moisture, and kept at 25±1° C. for 1-2 weeks before the fluid bait formulations were injected into the arena.

Feed medium comprised of 90% α-cellulose and 10% fine-ground Summon (FMC corp., Princeton, N.J.) was impregnated with 0.5% hexaflumuron (AI wt/wt) and homogeneously mixed with 1% methylcel solution to yield 10% dry weight feed medium in the resultant fluid termiticide bait formulation. Control fluid formulations were also prepared by using acetone-treated feed medium, i.e. 90% α-cellulose and 10% fine-ground Summon impregnated with acetone.

One to two weeks after placing termites in the arena, the wooden plug at the opposite end 45 of the Tygon tubing connection was removed and approximate 5-10 grams of the fluid bait formulation was injected into the main tunnel by using a syringe (0.3 cm diameter and 5 cm long). The injected quantity usually resulted in filling approximately 10-15 cm of the main tunnels with the fluid bait formulation.

Fifteen experimental units each were prepared for both treated and untreated control for *C. formosanus*, totaling 30 units. For *R. virginicus*, 12 experimental units each were prepared for both treated and untreated control, totaling 24 units. The experimental units were kept at 25±1° C. At 4, 6, and 8 weeks, each replicate of treated and untreated control was disassembled to count the number of surviving workers. Percent moralities were transformed to log (X+1) and subjected to t-test to compare the difference between treated and untreated control groups separately at 4, 6, and 8 week for each species.

Results

One to two weeks after being introduced into the arena, termites extensively fed on wood by expanding the provided tunnels as illustrated in FIG. 2. Termites were present in most of the tunnels when the fluid bait formulations were injected at one end 45, and some were trapped in the injected fluid bait, but most were able to free themselves the following day when the wood absorbed substantial amount of liquid and the feed medium became more solid. In the initial weeks after injecting the fluid bait formulation into the arena, termites moved the feed medium throughout the tunnel system, and by $3^{rd}$ week, some workers in treated arenas began to show symptoms of hexaflumuron effects, i.e., marbled coloration with sluggish movement. At the $4^{th}$ week, dead workers were found in the tunnels of treated arenas, and mortality was ca. 36% and 73% for *C. formosanus* and *R. virginicus*, respectively, which were significantly higher than untreated control groups (Table 1). The timing of the appearance of these symptoms and mortality was similar to the previous laboratory study with hexaflumuron baits (Su and Scheffrahn 1993). By $6^{th}$ week, mortalities for both species exceeded 90%. Control mortality of one *R. virginicus* colony exceeded 30% at $8^{th}$ week and data of this colony was excluded from the analysis. Mortality of the treated *C. formosanus* at $8^{th}$ week was 100%. Mean mortality of *R. virginicus* exposed to hexaflumuron at 8 week was ca. 96%, with a few survivors exhibiting hexaflumuron-affected symptoms, and eventually died after 8 weeks (Table 1).

The results showed that the fluid bait formulation being injected at one part of the tunnel system can be spread to the rest of the experiment unit to cause 90-100% mortality 6-8 weeks later. As demonstrated in previous laboratory and field studies (Su and Scheffrahn 1993, Su 1994, Su et al. 1995), the 6-8 weeks latent effect of hexaflumuron is long enough to enable termites to spread the AI-impregnated feed medium amongst the termites of the colony and eliminate the field colony that may extend to several hundred feet. When injected into an active gallery of termites in a structure, a tree or in soil, termites in the active sites should be able to carry the feed medium from the fluid bait formulation to feed the nestmates, leading to the elimination of a termite colony.

TABLE 1

Termite mortalities 4, 6, and 8 weeks after feeding on injectable baits treated with 0.5% hexaflumuron in laboratory arenas

| | C. formosanus | | R. virginicus | |
|---|---|---|---|---|
| Weeks | Control | Treated | Control | Treated |
| 4 | 15.4 ± 0.7a | 36.1 ± 3.8b | 17.4 ± 1.7a | 73.2 ± 3.4b |
| 6 | 19.4 ± 1.4a | 94.6 ± 3.9b | 23.7 ± 2.9a | 92.6 ± 6.0b |
| 8 | 16.7 ± 1.9a | 100.0 ± 0.0b | 17.2 ± 2.4a | 96.4 ± 1.2b |

Example II

Materials and Methods

Field efficacy of the fluid bait formulation was tested against a colony of *C. formosanus* infesting a tree (Sweetgum, *Liquidambar styraciflua*) in New Orleans. The infested tree was used as a surrogate of an above-ground infestation. Six holes (ca. 1.3 cm diameter) were drilled into the tree trunk at eye level to intercept termite galleries within. A fiber-optic scope was used to confirm termite presence in the holes. An in-ground monitoring station similar to that of Su and Scheffrahn (1986) was installed in soil near the tree. The station consisted of a plastic collar (18.5 cm diameter by 19 cm high) inserted into the ground and contained a feeding block composed of 18 spruce (*Picea* sp.) slices (13.4 cm by 8.3 cm by 0.4 cm) bound together with wires. Stations were examined monthly or bi-monthly to visually estimate % wood consumption, and the infested blocks were collected to count the number of termites. Numbers of drilled holes with live termites, % wood consumption and the number of workers in the in-ground station were used to represent termite activities.

Fluid baits were placed in plastic tubes (6 cm diameter and 17 cm long) and injected through two drilled holes on the tree by using caulking guns while termite activities were monitored from the other four drilled holes. Another tree (Bold cypress, *Taxodium distichum*), also infested by *C. formosanus* in New Orleans, served as the untreated control. Three drilled holes of the control tree intercepted termites, and one hole received fluid bait without hexaflumuron, while the other two drilled holes served as the monitoring loci. At the $3^{rd}$ inspection in September 2012 when continuous termite activities were confirmed in the infested trees, liquid baits were applied.

Results

Figure 3:
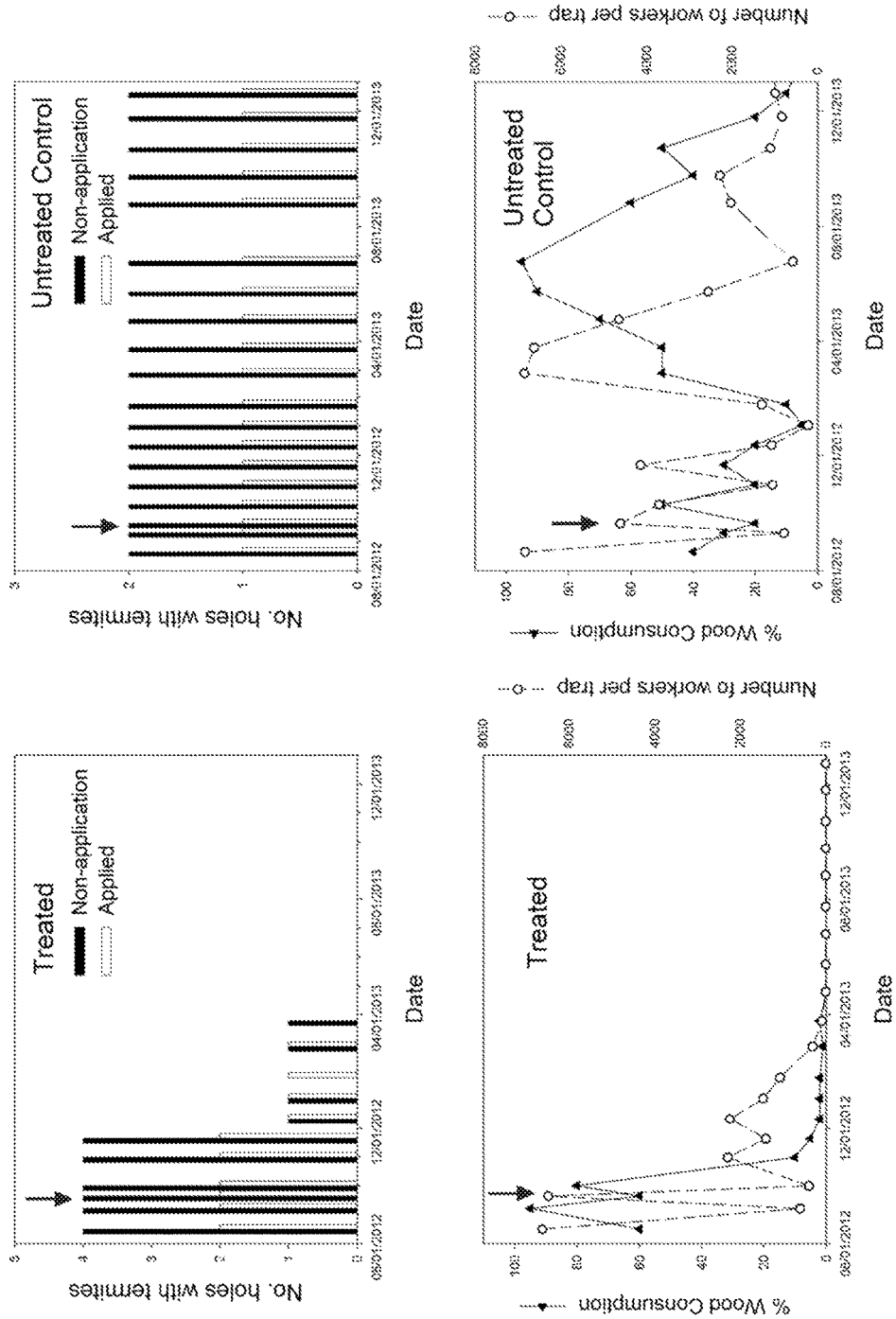
FIG. 3 illustrated changes in termite activities in drilled hole on tree trunk and in the in-ground monitoring stations (represented by the % wood consumption and the number of workers collected), following the application (arrows) of liquid baits (treated with 0.5% hexaflumuron) in trees infested with *C. formosanus*. Untreated control tree, also infested with *C. formosanus*, received similar liquid baits without hexaflumuron.

Through fiber-optic scope, live termites were found in all six holes (two received baits and four did not) up until December 2012, but wood consumption declined substantially in October; only one month after bait application (FIG. 3). The large fluctuation in the number of workers collected from the in-ground station resulted from the abandonment of station when, on some occasions, the feeding blocks were totally consumed. The overall trends of wood consumption rates and the numbers of collected termites, however, showed a general decline in termite activities in the station, as indicated by the low termite in the spring of 2013 when temperature began to rise (FIG. 3). The numbers of drilled holes with live termites also showed the same trend, i.e. a decline from six holes in December 2012 to 1-2 in the spring of 2013. Since May 2013, no live termites have been found in any of the six drilled holes or in the in-ground monitoring station with the feeding block untouched by termites. The trend of decline in treated tree was in sharp contrast with the termite activities recorded form the untreated tree. After the application of untreated baits in September 2012, termite activities (wood consumption rate and number of collected termites) did not change substantially except for a dip in December 2012 when the temperature fell (FIG. 3). As the temperature rose in the spring and summer of 2013, termite activities recovered with occasional fluctuation in the numbers of termites (i.e., due to station abandonment after the total consumption of feeding blocks), and live termites were found in all three drilled holes throughout the field trial period (FIG. 3). It is concluded that the application of treated fluid baits in September 2012 eliminated the *C. formosanus* colony by April of 2013.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

Esenther, G. R., T. C. Allen, J. E. Casida, and R. D. Shenefer. 1961. Termite attractant from fungus-infected wood. Science 134: 50.

Cornelius, M L, and A. Lax. 2005. Effect of Summon Preferred Food Source on feeding, tunneling, and bait station discovery by the Formosan subterranean termite (Isoptera: Rhinotermitidae). *J. Econ. Entomol.* 98:502-08

Rust, M. K., K. Haagsma, and J. Nyugen. 1996. Enhancing foraging of western subterranean termites (Isoptera: Rhinotermitidae) in arid environment. Sociobiology 28: 275-286.

Su, N.-Y. 1994. Field evaluation of a hexaflumuron bait for population suppression of subterranean termites (Isoptera: Rhinotermitidae). J. Econ. Entomol. 87: 389-397.

Su, N.-Y. 2007. Hermetically sealed baits for subterranean termites (Isoptera: Rhinotermitidae). J. Econ. Entomol. 100: 475-482

Su, N.-Y. and M. Lees. 2009. Biological activities of a bait toxicant for population management of subterranean termites. In. C. Perterson & D. Stout [eds.], pp. 87-96, Household, Structural and Residential Pest Management. Oxford University Press, NY.

Su, N.-Y., and R. H. Scheffrahn. 1986. A method to access, trap, and monitor field populations of the Formosan subterranean termite (Isoptera: Rhinotermitidae) in the urban environment. Sociobiology 12: 299-304.

Su, N.-Y. and R. H. Scheffrahn. 1993. Laboratory evaluation of two chitin synthesis inhibitors, hexaflumuron and diflubenzuron, as bait toxicants against Formosan and eastern subterranean termites (Isoptera: Rhinotermitidae). J. Econ. Entomol. 86: 1453-1457.

Su, N.-Y., E. M. Thoms, P. M. Ban, and R. H. Scheffrahn. 1995. A monitoring/baiting station to detect and eliminate foraging populations of subterranean termites (Isoptera: Rhinotermitidae) near structures. J. Econ. Entomol. 88: 932-936.

Su, N.-Y, P. M. Ban, and R. H. Scheffrahn. 1997. Remedial baiting with hexaflumuron in above-ground stations to control structure-infesting populations of the Formosan subterranean termite (Isoptera: Rhinotermitidae). J. Econ. Entomol. 90: 809-817.

Su, N.-Y., P. M. Ban, and R. H. Scheffrahn. 2001. Control of subterranean termites (Isoptera: Rhinotermitidae) using commercial prototype aboveground stations and hexaflumuron baits. Sociobiology 37: 111-120

Su, N.-Y., B. M. Stith, H. Puche, and P. Bardunias. 2004. Characterization of tunneling geometry of subterranean termites (Isoptera: Rhinotermitidae) by computer simulation. Sociobiology 44: 471-483.

I claim:

1. A fluid form bait formulation having a viscosity between 1 and 100 Pa·s, the formulation comprising a particulate feed medium impregnated with at least one active ingredient (AI) and suspended in a liquid carrier selected from methylcell solution, agar solution and gel solution;
wherein the feed medium is impregnated with the AI such that following dehydration of the formulation, a slow-acting and non-repellent concentration of the AI is present in the feed medium; and
wherein the AI is one or more insecticides selected from the group consisting of insect growth regulators and metabolic inhibitors.

2. The formulation of claim 1, where the feed medium comprises any one or more of the following materials selected from the group consisting of: α-cellulose, wood flour, and milled paper, wherein the feed medium is in fine powder form.

3. The formulation of claim 1, wherein the feed medium further comprises an attractant.

4. The formulation of claim 3, wherein the feed medium comprises fine powder form of wood materials decayed with brown-rot fungi or white-rot fungi.

5. The formulation of claim 3, wherein the attractant is a synthetic termite phagostimulant.

6. The formulation of claim 1, wherein the AI is selected from the group consisting of: hexaflumruon, noviflumuron, diflubenzuron, lufenuron, chlorfluazuron, bistrifluron, and triflumruon, and the ecdysone agonist is a ecdysteroid.

7. The formulation of claim 1, wherein the metabolic inhibitor is selected from the group consisting of: borates, sulfluramid, hydramethylnon, ivermectin, fipronil, imidacloprid, and thiamethoxam.

8. The formulation of claim 1, wherein the feed medium is α-cellulose, the liquid carrier is methylcell solution and the active ingredient is hexaflumuron.

9. The formulation of claim 1, wherein the viscosity of the formulation is between about 1-50 Pas.

10. The formulation of claim 1, wherein the viscosity of the formulation is between about 50-100 Pas.

11. The formulation of claim 1, wherein the impregnated feed medium is suspended in the liquid carrier to yield a 15-20% dry weight feed medium in 0.5% methylcell solution.

12. The formulation of claim 1, wherein the impregnated feed medium is suspended in the liquid carrier to yield a 10% dry weight feed medium in 1% methylcell solution.

13. The formulation of claim 1, wherein the insect growth regulator is a chitin synthesis inhibitor, juvenoid, or ecdyson agonist.

14. A method for controlling a termite infestation wherein said method comprises: providing a fluid form bait formulation according to claim 1; and injecting the fluid form bait formulation into a void in a structures created by termites.

15. The method of claim 14, wherein the fluid form bait formulation has a viscosity between about 1-50 Pa·s.

16. A kit for preparing a fluid bait formulation having a viscosity of between 1 and 100 Pa·s, wherein the kit comprises: a particulate feed medium impregnated with at least one active ingredient (AI), a liquid carrier to be mixed with the AI(s)-impregnated feed medium wherein the liquid carrier is selected from methylcell solution, agar solution and gel solution;
wherein the feed medium is impregnated with the AI such that following dehydration of the formulation, a slow-acting and non-repellent concentration of the AI is present in the feed medium; and
wherein the AI is one or more insecticides selected from the group consisting of insect growth regulators and metabolic inhibitors.

17. The kit of claim 16, further comprising an apparatus for injecting the liquid bait formulation into a termite infestation site.

18. The kit of claim 17, wherein the apparatus is a syringe.

19. The kit of claim 11, wherein the feed medium comprises 90% α-cellulose and 10% wood flour decayed with *G. trabeum* and is impregnated with hexaflumuron at 0.5% (AI wt/wt), wherein the liquid carrier is 1% methylcel solution.

20. The kit of claim 16, wherein the fluid form bait formulation has a viscosity between about 1-50 Pa·s.

* * * * *